United States Patent
Golde et al.

(10) Patent No.: US 7,789,268 B2
(45) Date of Patent: Sep. 7, 2010

(54) STERILIZABLE DISPENSER FOR STERILIZABLE LANCETS FOR BLEEDING MICE

(75) Inventors: William T. Golde, Cutchouge, NY (US); Peter Gollobin, Matinecock, NY (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 1405 days.

(21) Appl. No.: 11/097,199

(22) Filed: Apr. 1, 2005

(65) Prior Publication Data
US 2006/0086632 A1 Apr. 27, 2006

Related U.S. Application Data

(63) Continuation-in-part of application No. 10/967,796, filed on Oct. 18, 2004.

(51) Int. Cl.
*A47F 1/04* (2006.01)
(52) U.S. Cl. .................. 221/309; 221/56; 221/255; 221/257; 221/279; 221/287
(58) Field of Classification Search .............. 221/255, 221/257, 287, 46, 309, 279; 206/363; 600/583
See application file for complete search history.

(56) References Cited

U.S. PATENT DOCUMENTS

| 4,789,080 | A | | 12/1988 | Iten |
| 4,826,042 | A | | 5/1989 | Vujovich |
| 5,139,167 | A | | 8/1992 | McCarthy |
| 5,335,822 | A | * | 8/1994 | Kasper ................ 221/259 |
| 5,409,133 | A | | 4/1995 | Gringer |
| 5,536,472 | A | * | 7/1996 | Terashima et al. .......... 221/279 |
| 5,829,631 | A | * | 11/1998 | Kasper ................ 221/227 |
| 5,950,865 | A | * | 9/1999 | Menes ................ 221/232 |
| 6,763,972 | B2 | | 7/2004 | Graupner |
| 6,796,455 | B2 | | 9/2004 | Schmidt |

* cited by examiner

*Primary Examiner*—Gene Crawford
*Assistant Examiner*—Timothy R Waggoner
(74) *Attorney, Agent, or Firm*—John Fado; Evelyn Rabin

(57) ABSTRACT

An assembly for dispensing sterile lancets one at a time from a clip holding a plurality of lancets is described. The assembly is configured to dispense the lancets easily and conveniently under laboratory conditions where the lancet user is gloved and must manipulate the dispenser using only one hand while holding the animal being bled in the other. The assembly and its components are made of polycarbonate and rubber and are therefore capable of being sterilized by steam autoclaving methods or by other means of sterilization.

19 Claims, 12 Drawing Sheets

STERILIZABLE DISPENSER FOR STERILIZABLE LANCETS FOR BLEEDING MICE

The present application is a continuation-in-part of copending application Ser. No. 10/967,796 filed Oct. 18, 2004, which is hereby incorporated by reference in its entirety.

BACKGROUND OF THE INVENTION

1. Field of the Invention

This invention relates generally to a lancet dispenser assembly, and more specifically, to a lancet dispenser assembly composed of a base component, a clip component containing a plurality of disposable lancets for bleeding small animals, a rectangular, open-ended cover or chamber component enclosing the clip of lancets and serving to hold the clip and lancets during the sterilization process and to allow for maintaining the lancets until their transfer to the dispenser unit component, a dispenser unit component, wherein the clip is held after transfer from the cover component and from which the lancets are dispensed, one at a time, and a top weight component. An integral element of the dispenser unit component is a rubber escapement device which controls or directs the movement of the lancets allowing them to be released one lancet at a time. The dispenser unit is positioned on the base component of the dispenser assembly enabling the lancets to be removed easily. The entire lancet dispenser assembly can be sterilized.

2. Description of the Relevant Art

Biomedical research using small animal models has contributed tremendously to the improvement of human and animal health. Small animals, most prominently rodents, provide an inexpensive platform for biological investigation as well as testing procedures and pharmaceuticals for safety and efficacy. Use of laboratory rodents has become more carefully regulated over the past several decades to insure that animal care and use in the research setting is as humane as possible. Researchers in all aspects of biology and medicine are governed by institutional animal care and use committees (IACUC) that insure the most humane use of these animals as possible.

One very important aspect of rodent models in research is the acquisition of blood samples for testing. Because of the small size of the animals, drawing blood samples is a challenge to the investigator. A number of methods are employed that pass the review of an IACUC, but none are particularly humane or simple. For example, in the USA, the most common bleeding method is retro-orbital, puncturing the orbital sinus behind the eye. This method consistently yields a reasonable blood volume when the investigator is experienced and practiced. (2002. *Laboratory Animal Medicine*, 2$^{nd}$ Edition, Fox et al., eds., Elsevier Science, New York, N.Y.). However, this method is banned in a number of countries because it is not considered humane.

A second common method is cardiac puncture. This procedure requires anesthesia, which may alter parameters of the experiment. Briefly, a small gauge needle is inserted into the ventricle and blood is slowly drawn out. This procedure requires an extremely practiced investigator and often animals do not survive the process. Again, this procedure is not simple and is only humane when the procedure goes very well with minimal damage along the needle track. Because the chance of losing animals is so prominent, investigators often use an inflated number of animals to accommodate loss during an experiment.

A third more simple method of bleeding mice is the tail clip. A piece of the tail is excised and blood harvested from the severed tail vein. This can be done repeatedly for a few sequential bleeds. The draw back is, that in order to leave enough tail for multiple future bleeds, only a small piece of tail is cut yielding a small blood sample of only a few drops (0.1 ml). This method is easily done without anesthesia. However, this procedure may not be considered humane, especially for multiple blood draws.

Finally, a method which is more humane and done without anesthesia is the saphenous vein puncture (Hem et al. 1998. *Laboratory Animal* 32: 364-368). This is a more complicated and time consuming method that involves immobilizing the animal with the rear legs accessible. The hair is shaved from the thigh using a small scalpel or razor. The saphenous vein of the thigh is evident and can be punctured with a 23 to 25 gauge needle. Blood is collected with a microvette capillary collection tube. These vessels have a maximum volume of 0.3 ml. A compress is held on the site to stop the bleeding.

This is a very humane method of blood collection; and since no anesthesia is required, there are no side effects to consider. However, this procedure requires extensive time working with each animal and is not compatible with large trials of pharmaceuticals or biologicals. The man hours required to do a large trial, 50 to 100 animals, would cause researchers to design smaller experiments using fewer animals. The investigators describing this method limit the amount of blood collected to 0.3 ml and in practice, usually less. Therefore, this would yield approximately 0.1 ml of serum and limit analysis to a few very small volume assays.

Thus, there is a need for an improved humane method of bleeding mice where utilization of the method can lessen the need for using large numbers of animals to compensate for animal losses and where utilizing the method allows for testing the animal as often as necessary, including sampling more than one time per day, and yields blood samples of sufficient volume for testing all necessary parameters. The blood lancet of our original invention, Ser. No. 10/967,796, satisfies all the above needs; however, the individual packaging presents another problem. Very often, large numbers of animals are being bled and/or the animals are being bled in a laminar flow hood or in a glove-box. Under such conditions, individually-wrapped sterile lancets are neither convenient nor expedient to use. In these instances, while it is necessary that the lancets be sterile, they cannot be manipulated easily if they are individually wrapped. Thus, there is a need for a device to easily dispense unwrapped lancets where the device and lancets can be sterilized on site.

In the art related to blades, e.g., razor blades, utility blades, or microtome blades, a variety of apparatuses are known for dispensing a single blade at a time from a stack of blades. For example, U.S. Pat. No. 4,789,080 to Iten discloses a utility blade dispenser formed to expose the side edge of a utility blade while it is still at the bottom of the stack of blades within the dispenser, so that a sideways pushing force may be applied by a person's finger to separate this bottommost blade from the stack. U.S. Pat. No. 4,826,042 to Vujovich discloses a blade dispenser with a knob that a person slides to eject a blade from the dispenser. Similarly, U.S. Pat. No. 6,796,455 to Schmidt discloses a blade dispenser assembly which includes a housing and an integrally formed shuttle mechanism which functions to dispense one blade at a time from the bottom of a stack of blades held with the housing and U.S. Pat. No. 6,763,972 to Graupner discloses a microtome knife dispenser which comprises a housing for the reception of multiple knives arranged in a stack wherein a spring is arranged for biasing the knife stack against the inside of the housing cover and a slider is provided to travel with a groove on the outside of the housing cover for engaging an individual knife. Gringer (U.S. Pat. No. 5,409,133) discloses a blade dispenser which includes a housing having side and end walls which define a cavity for storing and dispensing razor blades wherein the open top of the dispenser includes rails along the tops of the sidewalls for guiding the blades out of the housing. A resilient arm integral with the housing is located below the razor blades for applying an upward force on the razor blades against the rails and for aligning a blade to be dispensed with the dispensing slot. McCarthy (U.S. Pat. No. 5,139,167) discloses a blade magazine for storing, transporting and dispensing individually a large number of single edge safety blades. The magazine is essentially an elongated rectangular box having an opening at the base of one wall and thumb-shaped recess along the bottom wall for dispensing a single blade at a time out of the slot in the bottom of the box. A small magnet is disposed on the outside wall and acts to stabilize the blades in the magazine and also to assist in dispensing.

These devices are not suitable devices for dispensing lancets for bleeding mice under such conditions where many animals are being bled or where the bleeding is taking place under, for example, glove box conditions because of a variety of deficiencies with respect to dispensing the lancets of the invention. For example, the dispenser of Iten (U.S. Pat. No. 4,789,080) exposes the side of the utility blade and the blade is removed from the bottom of the stack. These properties preclude utilizing such an apparatus to dispense the lancet of the invention. A quality of the lancet of the invention is that it is manufactured from extremely clean degreased steel; therefore, an additional accommodation or element is required to allow them to become separable. The dispenser of Vujovich requires a knob which one slides to eject the blade; however, one-handed manipulation is required to obtain a single lancet when bleeding animals under laboratory conditions described above because the other hand is usually holding the animal being bled. The dispenser of Vujovich precludes such manipulations, as do the dispensers of Schmidt, Graupner, Gringer, and McCarthy. Such devices are not suitable for dispensing the lancets of the invention because said dispensers have integral parts, e.g., sliders and springs, resilient arm and rails, and magnets, which cannot be used with the lancets of the invention and which are not convenient to use in the laboratory environment. In addition, these dispensing devices do not allow for easy retrieval of lancets of the design of the invention and may be compromised by the process of steam sterilization required for use in animal colonies or isolation hoods.

Thus, while various dispensing devices have been developed to dispense various types of blades one at a time, there still remains a need in the art for a more effective device for dispensing a lancet of the design of the invention for using in bleeding laboratory animals under laboratory conditions. Under such conditions, where large numbers of animals are bled at a time, e.g., for archival or validation purposes or where this involves bleeding large numbers of animals in a hood or glove-box and where laboratory personnel are wearing protective (e.g., rubber, latex, etc.) gloves, sterile lancets must be easily obtainable using only one hand. To date, there is no lancet dispensing apparatus that conveniently and expediently dispenses sterile lancets suitable for bleeding animals, particularly mice. Therefore, a lancet dispenser and associated lancet clips which can be easily sterilized by steam autoclave or other means, which is both convenient and safe to use in a laboratory environment, and which allows for the removal and reloading of lancets easily while wearing gloves and using only one hand, is needed.

The present invention described below solves the drawbacks related to prior art devices currently used for dispensing blades.

SUMMARY OF THE INVENTION

We have discovered a device for dispensing sterile lancets which can be used in a laboratory setting thus making it possible to obtain blood samples from small animals conveniently, expediently, and under sterile conditions In accordance with this discovery, it is an object of the invention to provide a dispensing device for use in a contained sterile environment for effectively, conveniently, expediently, and safely dispensing sterile lancets of the invention, one lancet at a time.

It is also an object of the invention to provide a device which exists in parts, each part having a particular function and each part being capable of being disassembled and reassembled and of separately being cleaned and sterilized so that sterility can be maintained in the contained laboratory environment.

An additional object of the invention provides for a component which is a base, a component which is a clip and cover containing a plurality of disposable lancets for bleeding mice and each lancet having a flat point 4.0 to 6.0 mm in length, and a component which is a rectangular, open-ended dispensing unit enclosing the clip of lancets allowing for maintaining the integrity of the lancets while safely dispensing individual lancets from a stack of lancets stored within the cavity of the dispenser unit component.

A further object of the invention provides for an entire lancet dispenser assembly which can be sterilized as an entire unit and/or each component, i.e., the base, clip containing lancets, cover, top weight, and dispenser unit can be sterilized individually or in containers enclosing a plurality of components.

Yet a further object of the invention provides for a dispenser assembly which can be easily used by an individual wearing latex, latex-type, or vinyl gloves, as are utilized in a laboratory setting, including in a sterile glove-box environment, to remove lancets one lancet at a time quickly using only one hand.

Other objects and advantages of this invention will become readily apparent from the ensuing description.

BRIEF DESCRIPTION OF THE DRAWINGS

FIG. 11A depicts a lateral view of an empty dispenser unit; no clip or lancets are in position within the cavity of the dispenser unit. FIG. 11B depicts a lateral view of the dispenser unit 400 showing a clip in position within the cavity. The clip housing is visible in the cavity; stacked lancets are shown in position in the bottommost portion of cavity. In FIG. 11C, when the clip is in position within the cavity of the dispenser unit, the bottommost individual lancet is capable of being directed along an exit pathway, the upper surface of the bottommost lancet being directed along the surface of the next lancet, and being further directed in a horizontal direction to contact the escapement device resulting in the individual lancet being dispensed into the index finger and thumb of the lancet user.

DETAILED DESCRIPTION OF THE INVENTION

The apparatus of this invention is a dispensing device designed for dispensing lancets one at a time quickly and conveniently. While not being limited thereto, the device is especially suited for use with the lancet described in Ser. No. 10/967,796 filed Oct. 18, 2004, which is herein incorporated by reference, wherein said lancets are designed for use in a rapid and humane method for drawing blood samples from small animals.

The method of the invention involves bleeding mice from the submandibular vascular bundle located at the rear of the mouse jaw (cheek pouch) using the lancet device of the invention. The lancet device of the invention is based on the standard lancet used for obtaining small blood samples from humans; however, the point length of the standard lancet, 3.0 mm, is too short for use in the mouse procedure. Therefore, 4.0 mm, 5.0 mm, and 5.5 mm lancets were produced and tested. The lancet's design controls the depth of the skin punch such that there is a high level of consistency. Blood volumes collected are always greater than 0.3 ml and bleeding is arrested once a sufficient volume was collected. The 4.0 mm lancets work very well on young mice, 2-6 weeks old; the 5 mm lancets, on mice 2-6 months old; and 5.5 mm lancets work best on mice over 6 months old.

Thus, referring to FIGS. 1-4, an effective lancet, as described in Ser. No. 10/967,796, filed Oct. 18, 2004, is a metal lancet, made from corrosion resistant stainless steel, its flat point having one or two sharpened edges. Said lancet is a hand-held, disposable, elongated metal, generally flat lancet, having a handle portion 12 at one end and a flat V-shaped point 14 at its other end; said lancet has the following general dimensions: the flat point can range in length from 4.0 mm to 6.0 mm, depending on the size of the animal. The overall length can range from 20 mm to 60 mm; the width can range from 2.0 to 15.0 mm. The lancet is most desirably provided with a set of raised knurls 13 or a raised ridge along the handle portion to aid in manipulating the device and to add stiffness if thin metal is used. The thickness of the lancet, excluding the raised portion, is ideally in the range of 0.076 mm to 0.381 mm.

Figure 1:
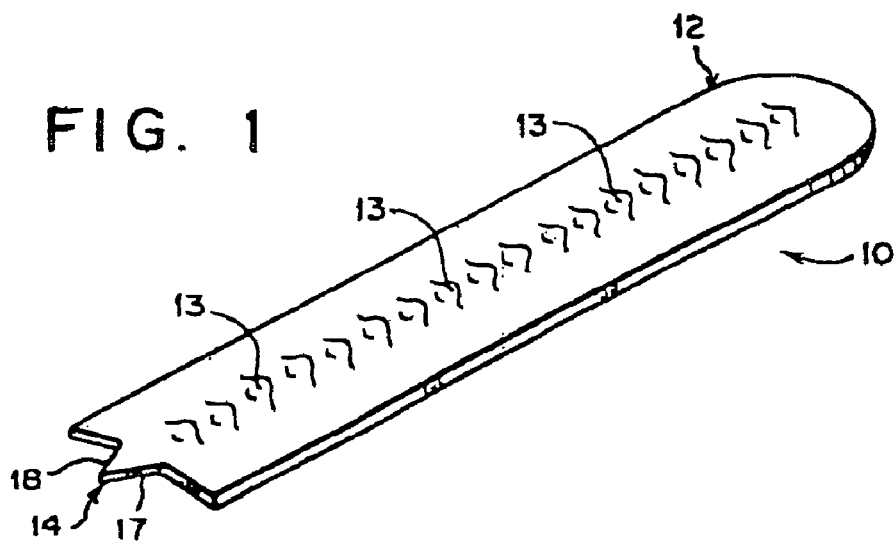
FIG. 1 is a perspective view of the disposable lancet 10 used in the present method.
Figure 2:
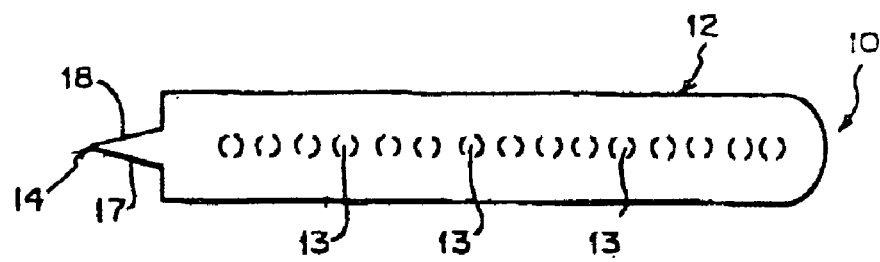
FIG. 2 is a top elevational view of the disposable lancet 10 used in the present method.
Figure 3:
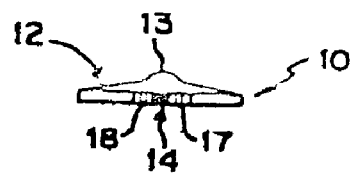
FIG. 3 is a left side elevational view of the disposable lancet 10 used in the present method.
Figure 4:
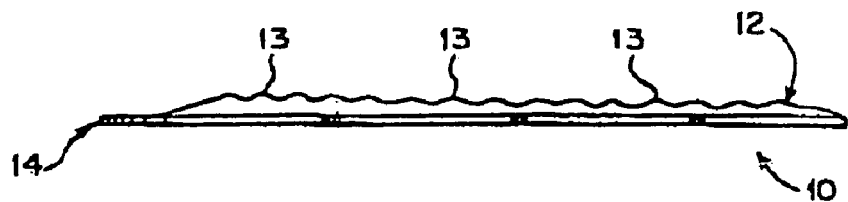
FIG. 4 is an elevational view of the longer side of the disposable lancet 10 used in the present method.
Figure 5:
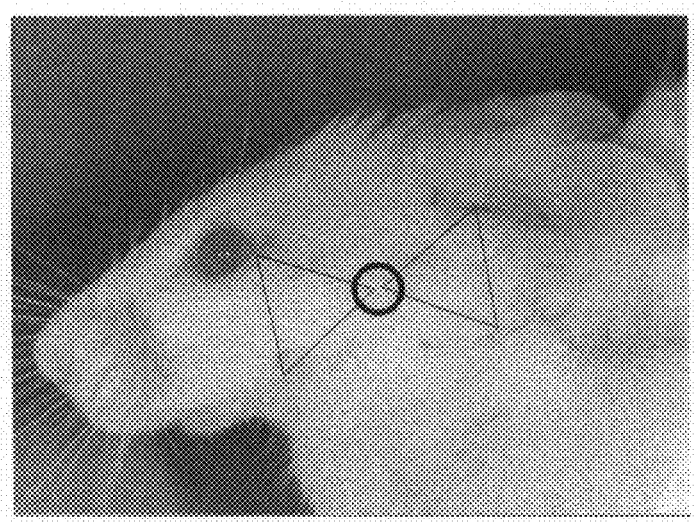
FIG. 5 depicts the area at the rear end of the jaw (cheek pouch) wherein a vascular bundle draining the submandibular and cranial regions, a convenient and consistent source of blood, is located.

The mouse lancet of Ser. No. 10/967,796, eliminates the problems experienced when bleeding from the submandibular vein with either a scalpel or needle. The animal is held securely in one hand, and using said lancet with the other hand, the cheek facing the investigator is punched with enough force to poke a small stick hole. When firm pressure is applied during the stick, sampling is very consistent for even occasional or inexperienced investigators performing the procedure. The position of the punch is critical to get a sufficient volume of blood in a very short time (see FIG. 5). The design of the lancet ensures that the animal does not experience a cut all the way through the inside of the cheek pouch and that a sufficient volume of blood is obtained humanely. This provides the researcher with the confidence to push hard enough so that too light a touch is no longer a problem. The lancets of Ser. No. 10/967,796 are sterile to eliminate cross-contamination between animals and can be individually wrapped. The lancets are relatively inexpensive; thus, they are more likely to be used on only a single animal.

Using this system, the same mouse can be bled daily as well as several times in a day. The volume of blood harvested when doing multiple bleedings in a day or daily bleeding should be adjusted to the total daily volumes recommended for animal safety and health for that size animal. The lancet device and method disclosed in Ser. No. 10/967,796 also allow for relatively rapid processing of many animals compared to the saphenous vein bleeding method where each animal must be shaved. An additional advantage is that there is no need for anesthesia, eliminating both effects on animal physiology and the need to tend to animals as the anesthetic wears off.

Compared to all mouse bleeding methods approved by IACUC guidelines, using said mouse lancet for cheek pouch bleeding, i.e., bleeding from the submandibular vascular bundle, is by far the most humane, efficient, and economic method for bleeding laboratory mice. This style of lancet has been used for decades to draw blood from many mammalian species, especially humans, and results in very little pain and discomfort. Animal activist groups, concerned with the treatment of research animals, object to the current methods of drawing blood from small animals. Such groups should not have any objections to the use of the same type of lancets which are used for fingertip blood samples from humans.

The utilization of this method and this particular lancet can improve scientific design and results in studies using laboratory mice and may be applied to other laboratory animals including rats, hamsters and gerbils.

The lancets and method of bleeding mice of the invention allows for testing the animal as often as necessary, including sampling more than one time per day, and yields blood samples of sufficient volume for testing all necessary parameters. When large numbers of animals are bled at a time or when bleeding animals involves bleeding large numbers of animals in a hood or glove-box, laboratory personnel are wearing protective (e.g., rubber, latex, etc.) gloves and the lancets must be easily obtainable. The lancets cannot be manipulated easily if they are individually wrapped, and additionally, large and impracticable amounts of opened wrappers are generated.

This invention relates generally to a lancet dispenser assembly, and more specifically, to a lancet dispenser assembly composed of a base component; a clip component containing a plurality of disposable lancets; a rectangular, open-ended cover component enclosing the clip of lancets and serving to hold the clip and lancets during the sterilization process and to allow for maintaining sterility of the lancets until their transfer to a dispenser unit component; a dispenser unit component, wherein the clip is held after transfer from the cover component and from which the lancets are dispensed, one at a time; and a top weight. An integral component of the dispenser unit component is a rubber escapement device, a mechanical device that controls or directs the movement of the lancets allowing them to be released one lancet at a time. The dispenser unit is positioned on the base component of the dispenser assembly enabling the lancets to be removed easily. The components of the dispenser assembly are polycarbonate and rubber; the entire lancet dispenser assembly can be sterilized by steam autoclaving methods or by other means of sterilization.

The present invention provides embodiments of a dispenser assembly or apparatus that is suitable for dispensing lancets of the invention. As used herein, the term "lancet", with regard to that being dispensed in the dispensing assembly of the invention, includes, in addition to the lancet of the invention described above and in Ser. No. 10/967,796, other lancets that are relatively of a similar shape. In other words, it is not intended that the appended claims be limited in scope to lancets of the invention. Those skilled in the art will be able to recognize other examples of lancets that may suitably be used in conjunction with the present dispenser.

Figure 6:
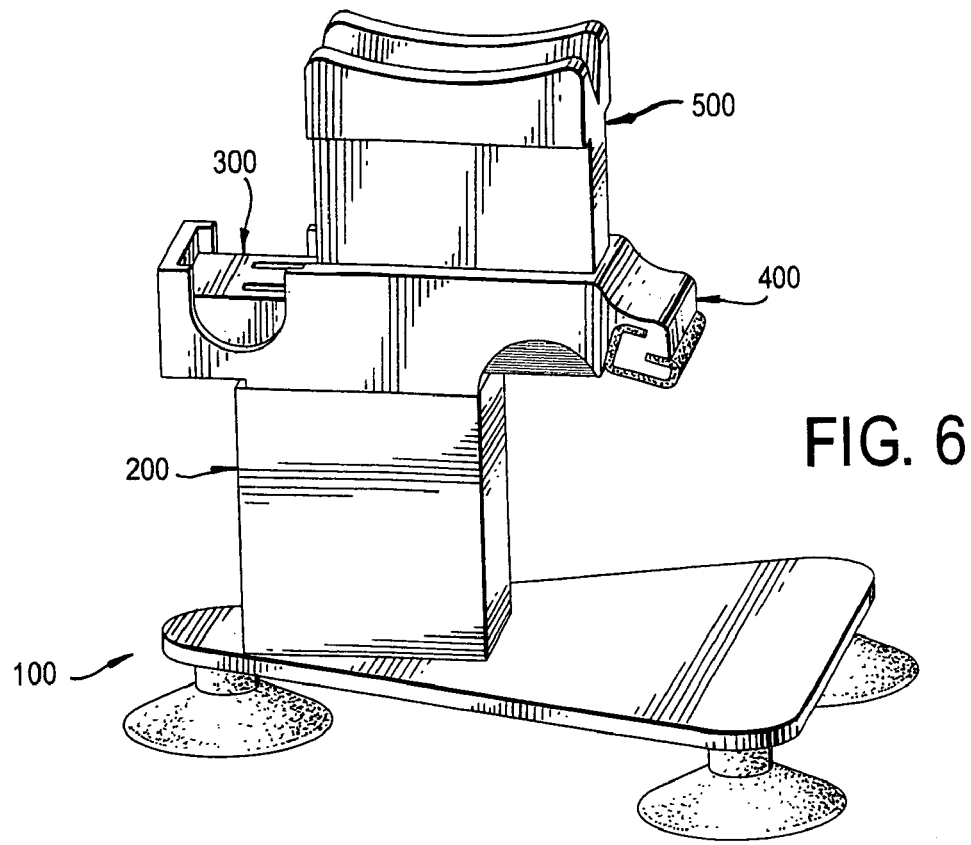
FIG. 6 is a view of the lancet dispensing assembly comprising a base component, a clip component, a dispenser unit component, and a top weight component.

In the drawings, reference numeral 100 generally denotes a lancet dispensing assembly according to the present invention. The assembly 100 comprises a base component 200, a clip component 300, a dispenser unit component 400, and a top weight component 500. An additional component integral to maintaining the clip component is a cover component 600. FIG. 6 depicts an embodiment of a lancet dispensing assembly 100 ready for use, wherein the lancet dispensing assembly 100 comprises base component 200, clip component 300, dispenser unit component 400 and top weight component 500.

Referring to FIG. 6, the principal components of the lancet dispensing assembly include: a base; a clip containing a plurality of disposable lancets; a dispenser unit, wherein the clip is held after transfer from the cover and from which the lancets are dispensed, one at a time; and a top weight. An integral element of the dispenser unit is a rubber escapement device which controls or directs the movement of the lancets allowing them to be released one lancet at a time.

Figure 7A:
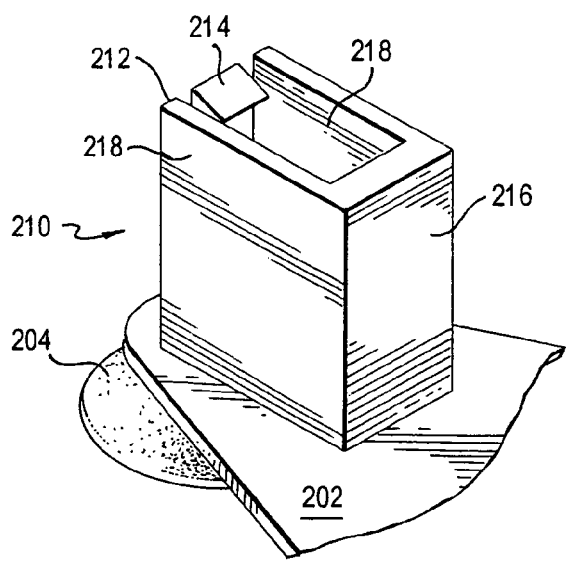
FIG. 7A depicts the tower support of the base component of the lancet dispenser assembly. Slits in the back wall of the tower support component (FIG. 7B) form a flexible latch which ensures easy insertion and extraction of the attachment element positioned on the bottommost surface of the dispenser unit component.
Figure 7B:
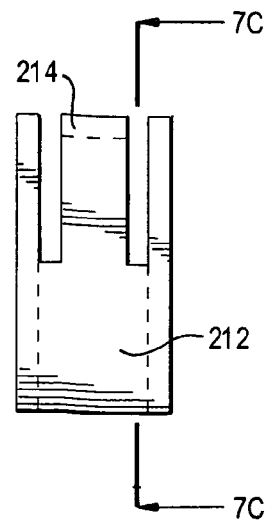
FIGS. 7C and 7D depict a side view and the front wall of the tower support, respectively, prior to insertion of the attachment element into the tower support.
Figure 7C:
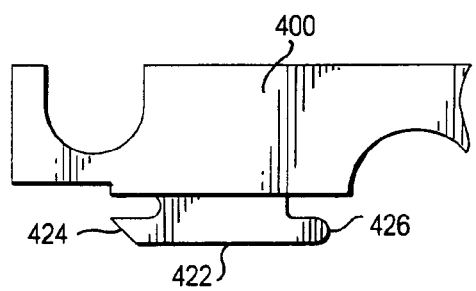
Figure 7C:
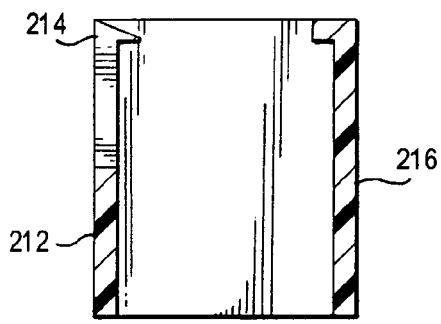
Figure 7D:
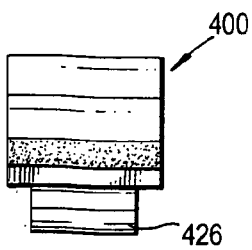
Figure 7D:
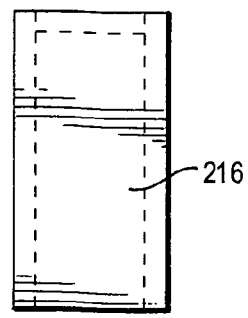

Base 200 is comprised of a bottom plate 202 as shown in FIG. 7A. Bottom plate 202 can be of any size or shape; the embodiment of FIG. 6 depicts bottom plate 202 to be three-sided and of a triangular shape. Bottom plate 202 is provided with at least one tower support 210 extending perpendicular from the upper surface of bottom plate 202 (FIG. 7A). The term bottom plate is intended to mean any wall or plate of the dispensing assembly on which one or more tower supports 210 are located. Tower support 210 is a rectangular column comprised of back wall 212 (FIGS. 7A and 7B), front wall 216 (FIGS. 7A, 7C, and 7D), and two side walls 218 (FIG. 7A). Tower support 210 holds the dispenser unit in position. Back wall 212 of tower support 210 is slit to form flexible latch 214 (FIGS. 7A-7C) to allow for easy insertion and extraction of the attachment element located at the base of the dispenser unit (as depicted in FIGS. 7C and 7D). Engagement of the attachment element results in the stable positioning of the dispenser unit in the tower support. Suction cups 204 (FIG. 7A) or the like, i.e., rubber matting or a device having similar friction-producing properties, are attached to the bottom surface of the bottom plate 202 to provide stability during the dispensing process. In another embodiment, the base could be weighted to provide such stability.

Figure 8A:
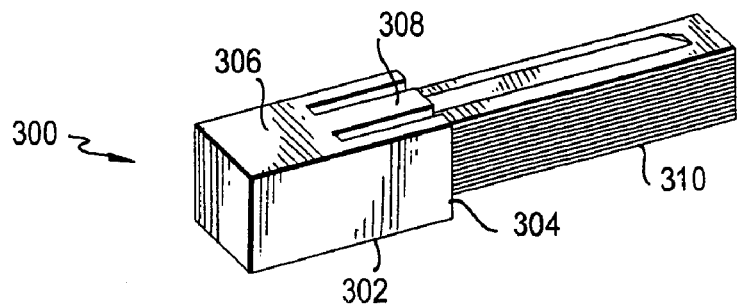
FIG. 8A shows the clip and FIG. 8B, its cover. Slits in both the upper and lower surfaces of the clip form flexible latches to securely hold the lancets during transport and during insertion into the dispenser unit component but allow easy removal of the lancets from the clip. The cover fits over the clip and has grooves along the inner lateral surface of the cover to ensure a tight, but releasable fit.

Clip component 300 (FIG. 8A) is an advantageously removable component which is configured to ensure that lancets remain in an orderly stack within the dispenser unit for problem-free dispensing. Additionally, a plurality of removable sterilizable clip components ensures the easy availability of sterilized lancets conveniently ready for use. Clip housing 302 (FIG. 8A) is configured to be rectangular and to have outer dimensions to allow for clip 300 to be positioned within the cavity of dispenser unit 400. The rectangular housing 302 of clip 300 is comprised of a portion having an interior cavity 304. Interior cavity 304 must be suitably configured to retain lancets in a substantially orderly stack, particularly when clip 300 is in position within the cavity of dispenser unit 400, so that each lancet is capable of being directed along a pathway through the cavity and delivered to lancet user. In the embodiment depicted in FIG. 8A, interior cavity 304 of clip housing 302 is configured to hold a predetermined number of lancets, e.g., fifty, in a stack configuration, the flat V-shaped pointed end being held within interior cavity 304 of clip housing 302. The interior bottom portion of clip housing 302 is configured so that there is no contact with the sharp points of the lancets so as to maintain their sharpness. The upper wall 306 and opposite bottom wall of interior cavity 304 are slit to form flexible latches. Flexible latch 308, shown on upper wall 306 in FIG. 8A, can be configured on said upper wall only or on both upper and bottom walls. Flexible latch 308 ensures flexibility and give, thus contributing to a means to hold the full stack of lancets while still allowing for the lancets to be separated and dispensed one at a time.

Figure 8B:
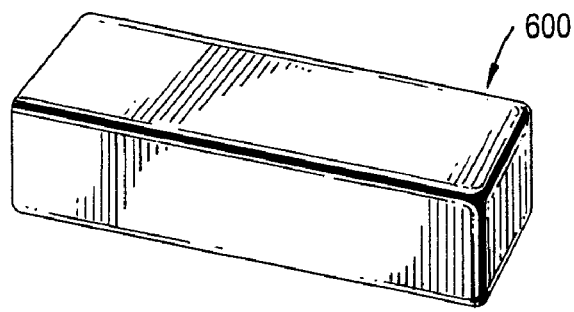

Clip component 300 containing a stack of lancets 310 of a predetermined set number to be held in place within the interior cavity 304 of housing 302 is configured to fit into cover 600 (FIG. 8B) for sterilization and transport. Cover 600 serves as a chamber for holding the clip and lancets during sterilization and for transport of the clip and lancets prior to their positioning within the dispenser unit. In the embodiment shown, the internal surface of cover 600 has one raised groove in the center of each opposing side and both grooves press against the clip when the clip is inserted into the cover to hold the clip within the cover. When the cover's adjacent sides are pressed together, the raised grooves flex away from the clip to allow for the clip's easy removal from the cover.

Referring to FIGS. 9-12, dispenser unit 400 is comprised of horizontally elongated housing 402, having side walls 404, end walls 406, and bottom wall 408, configured to form an essentially rectangular cavity 410 having inner dimensions which allow for clip 300 to be positioned within cavity 410 from the completely open top of dispenser unit 400. Cavity 410 is comprised of two rectangular portions of differing widths; namely, a wider portion configured to allow for rectangular housing 302 of clip 300 to be positioned in the cavity and a narrower portion configured to allow for the lancets to be positioned securely. The bottommost element of dispenser unit 400 is an attachment element 422 which holds dispenser unit 400 in position in tower support 210, facilitating removal of lancets one at a time by providing stability during the dispensing process. A bottom portion of cavity 410 is open to the outside, forming a rectangular opening adjacent to attachment element 422. One end of dispenser unit 400 is configured with a groove in which a rectangular rubber pad, escapement device 418, is held in place.

Figure 9:
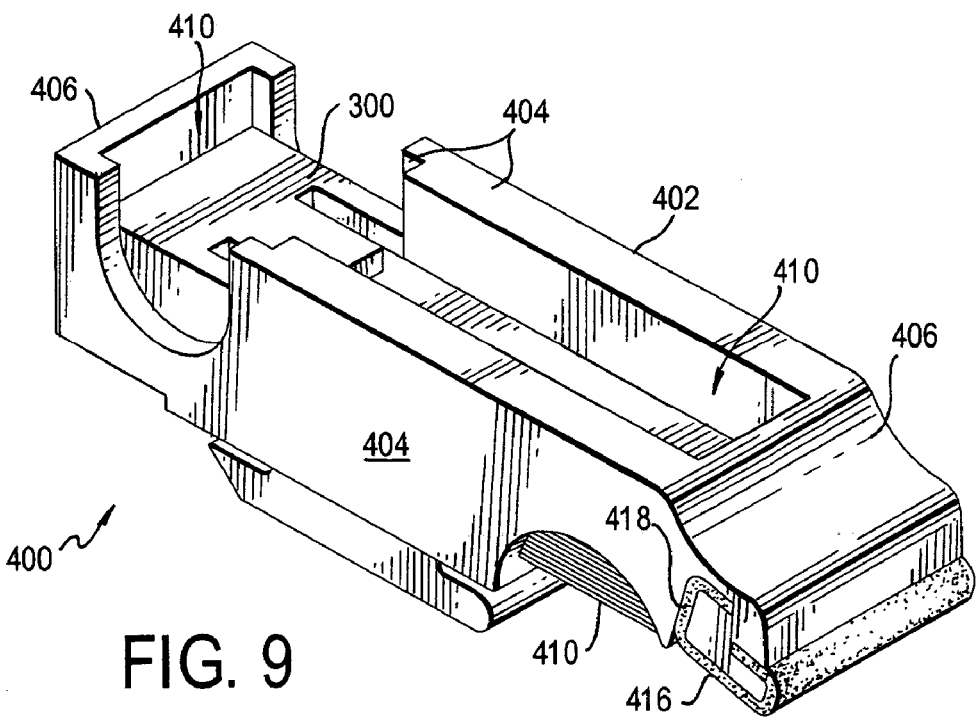
FIG. 9 is an elevational view of the longer side of the dispenser unit component with the clip component in position. The integral element of the dispenser unit component, the rubber escapement device, is shown.
Figure 10:
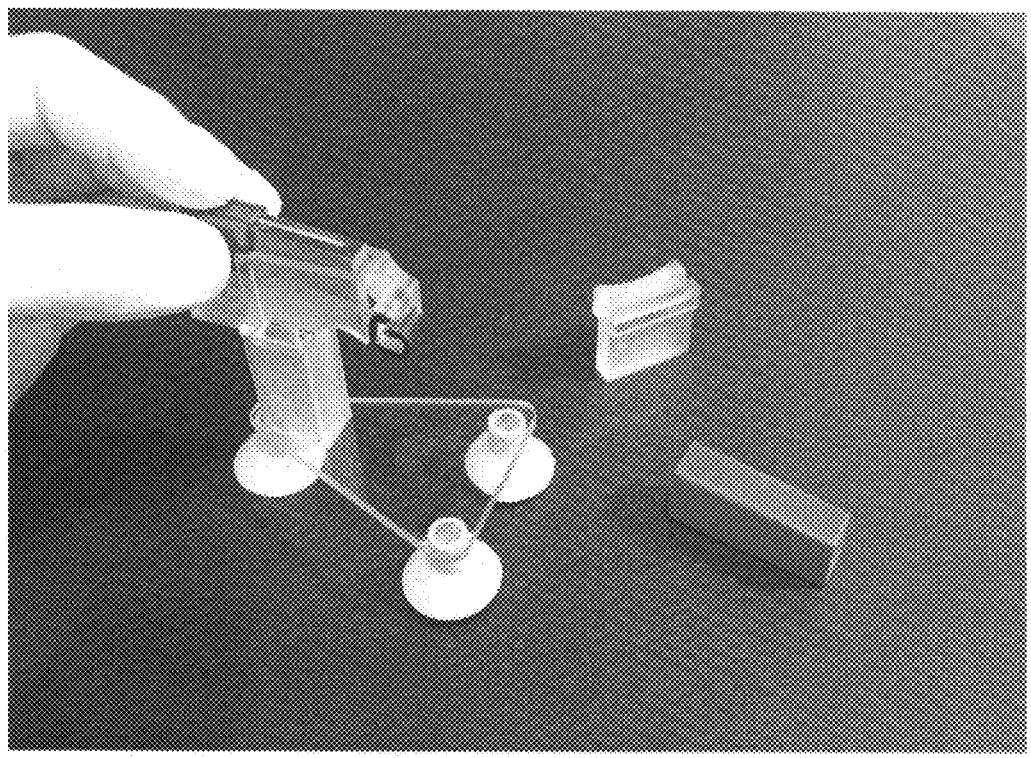
FIG. 10 shows the clip being inserted into the top of the dispenser unit component; the dispenser unit component in position, having been previously inserted into the tower support component of the base.
Figure 11A:
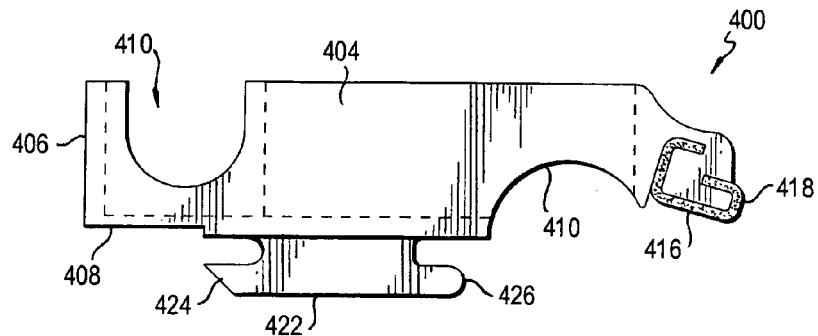
FIGS. 11A-C are lateral views of dispenser unit 400 under different conditions with regard to presence or absence of lancets and movement of lancets.
Figure 11B:
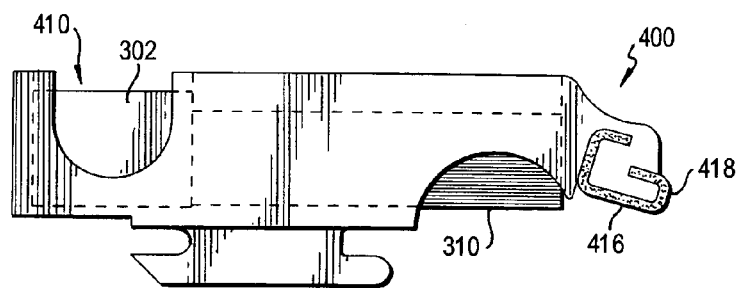

FIG. 9 depicts clip 300 in position within cavity 410; the stacked lancets residing within the clip are visible from this viewpoint, and can be seen in FIG. 11B. Also shown are side walls 404 which form a channel when the clip and lancets are in place. Escapement 418 and receiving surface 416 of escapement 418 are also shown. The insertion of clip 300, containing stacked lancets, into 410 of dispenser unit 400 is shown in FIG. 10.

Figure 11C:
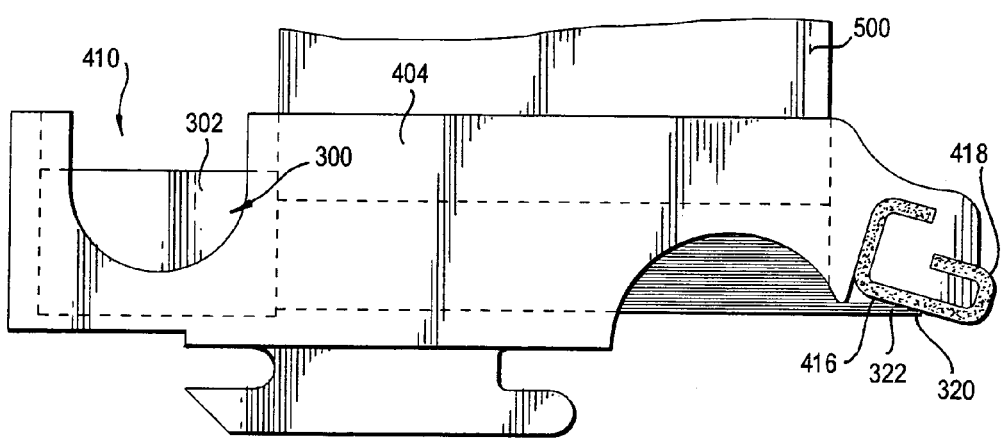

FIGS. 11A-C are lateral views of dispenser unit 400 under different conditions with regard to presence or absence of lancets and movement of lancets. FIG. 11A depicts a lateral view of an empty dispenser unit; no clip or lancets are in position within cavity 410 of the dispenser unit. Escapement device 418 and receiving surface 416 of escapement 418 are shown. A lateral view of attachment element 422 with back engagement contact 424 and front engagement contact 426 is also shown.

FIG. 11B depicts a lateral view of dispenser unit 400 showing a clip 300 in position within cavity 410. Housing 302 is visible in cavity 410; stacked lancets are shown in position in the bottommost portion of cavity 410, adjacent to receiving surface 416 of escapement 418.

Figures 12A, 12B:
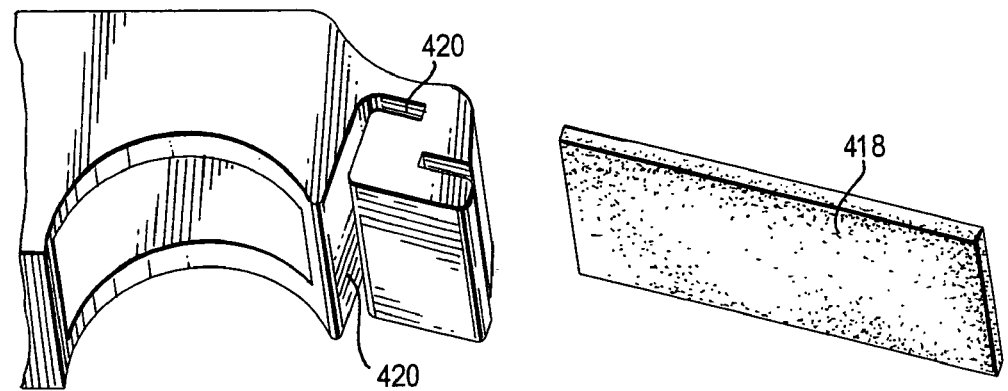
FIG. 12A is an end view of the dispenser unit component showing the groove wherein the rubber escapement, FIG. 12B, will be inserted.

In FIG. 11C, when clip 300 is in position within cavity 410 of the dispenser unit, the bottommost individual lancet is capable of being directed along an exit pathway. The cutout of side walls 404 enable the user to remove a single lancet by sliding said bottommost individual lancet 320 with the index finger, the upper surface of the bottommost lancet being directed along the surface of the next lancet 322, and being further directed in a horizontal direction to contact escapement 418 along its surface 416 resulting in the individual lancet being dispensed into the index finger and thumb of the lancet user. An enlargement of groove 420 and escapement 418 (removed from the groove) is shown in FIGS. 12A and 12B, respectively. Escapement device 418 is made of rubber or a similar frictional material.

Figure 13:
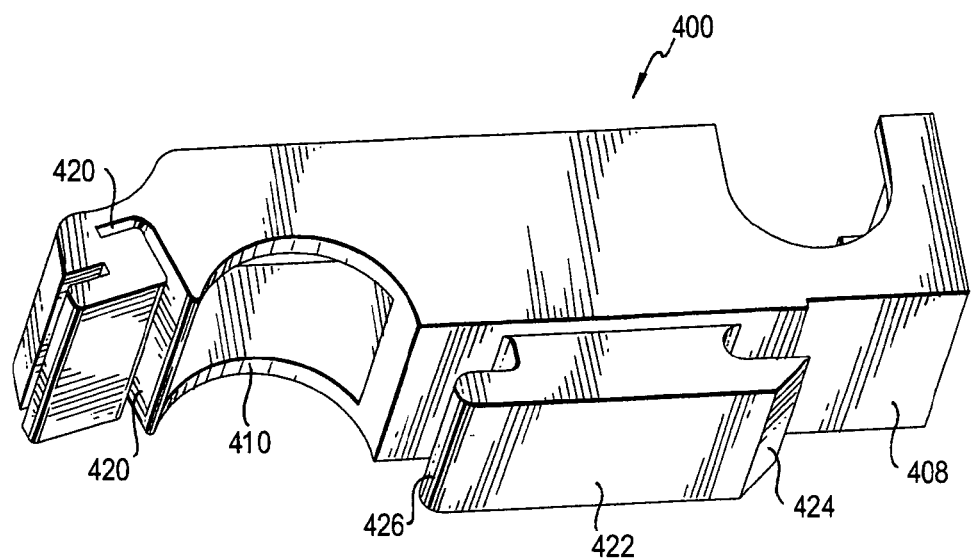
FIG. 13 is a bottom view of dispenser unit component showing a bottom view of the attachment element; the empty groove where the rubber escapement device resides is shown as is the channel through which the lancet is withdrawn.

FIG. 13 shows bottom wall 408 of dispenser unit 400 and the bottommost portion of cavity 410. The dispenser unit is empty; no clip or lancets are positioned within the cavity. Groove 420 is shown, without escapement 418 in place. Engagement contacts 424 and 426 of attachment element 422 are also shown. Dispenser unit 400 is positioned in tower support 210 (FIGS. 7A-7D) by means of attachment element 422, configured with back engagement contact 424 and a front engagement contact 426. As shown in FIGS. 7A and 7C, dispenser unit 400 is positioned in the tower support 210 by inserting front engagement contact 426 under the lip formed by front wall 216 of tower support 210, followed by snapping back flexible latch 214 of back wall 212.

Figure 14:
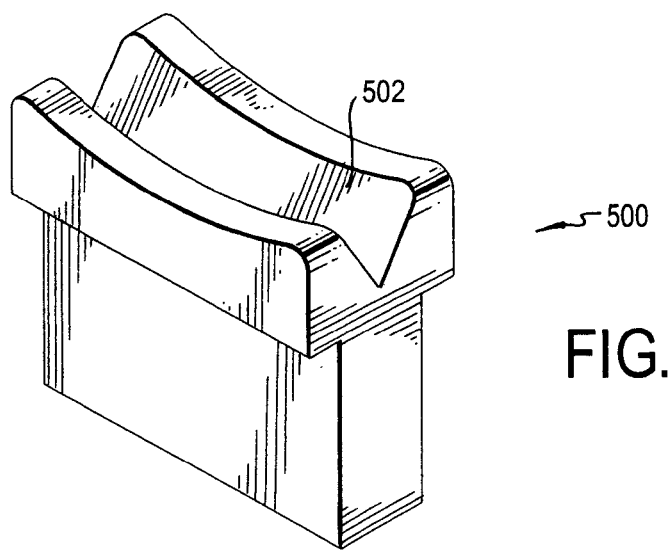
FIG. 14 is a depiction of the top weight with a groove where an individual may choose to position his or her thumb during the first steps of removing a lancet or where a dispensed lancet may be placed if necessary, without compromising the integrity of the point.

Top weight component 500 (FIG. 14) is configured to be positioned within cavity 410 subsequent to clip 300 being inserted into the completely open top of the dispenser unit component (as in FIG. 6). Top weight 500 rests on top of the lancets and holds the stack of lancets in place. As lancets are depleted from the dispenser unit, top weight 500 descends into the cavity. Groove 502 on the upper surface of top weight 500 serves both as a place where an individual may choose to position his or her thumb during the first steps of removing a lancet or where a dispensed lancet may be placed if necessary for convenience, or in those circumstances where two lancets may have been removed at the same time, without compromising the integrity of the point.

Figure 15:
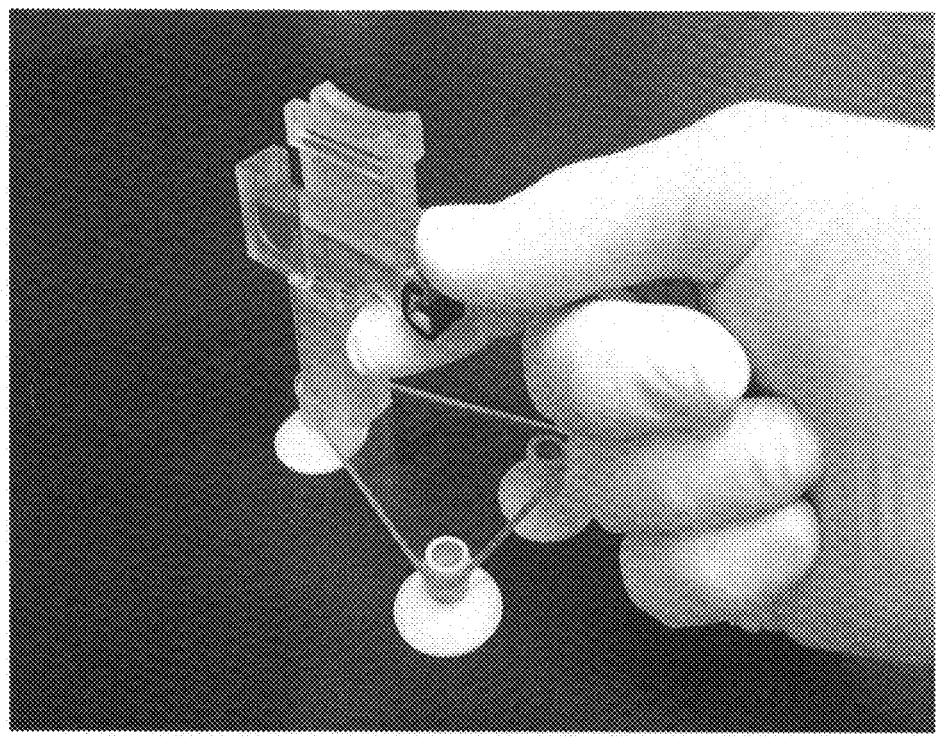
FIG. 15 shows a gloved index finger of an individual pushing up on the bottommost lancet, thus causing friction between the lancets and the rubber escapement device resulting in a single lancet being released from the stack of lancets. The top weight is seen in position. The individual's thumb sits on the uppermost surface of the dispenser unit; the thumb can also rest on the upper surface of the top weight.
Figure 16:
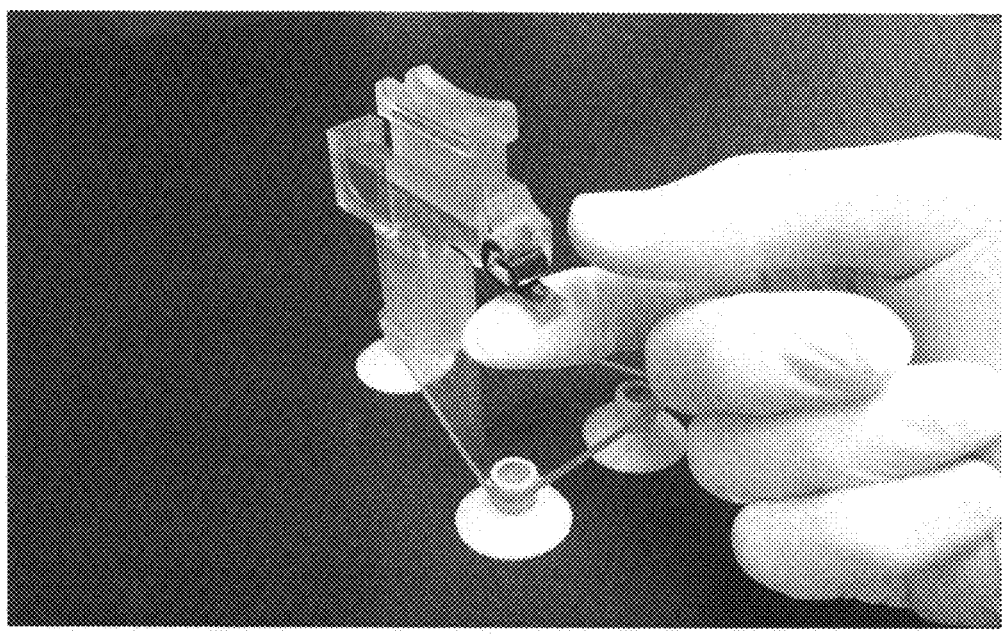
FIG. 16 shows a gloved index finger of an individual continuing to push up on the lancet, causing friction between the lancets and the rubber escapement device resulting in a single lancet being directed through the exit portal in the dispenser unit and in contact with the gloved forefinger.
Figure 17:
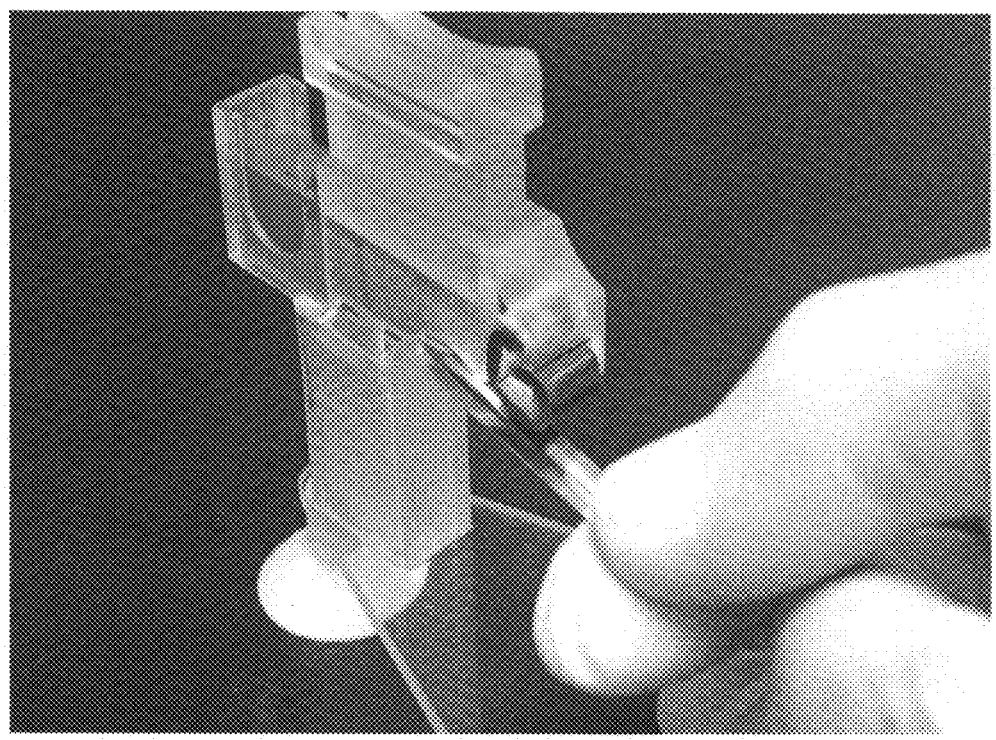
FIG. 17 shows a gloved index finger and thumb of an individual pulling the end of a single lancet from the dispenser unit.

In the embodiment illustrated in FIGS. 15-17, lancets are manually advanced to receiving surface 416 of escapement 418, as previously depicted in FIGS. 11A-C. As shown in the embodiment depicted in FIG. 15, the space within housing 402 restricts the movement of stacked lancets to only one direction, which is horizontally toward the dispensing end. The movement of the lancets is directed by the user's index finger to contact escapement 418 and a single lancet is advanced (FIG. 16). FIG. 17 shows the lancet being pulled from the dispenser unit by the user's index finger and thumb. The entire operation of removing the lancet can be managed with one hand, while holding the animal to be bled, in the other hand.

Figure 18:
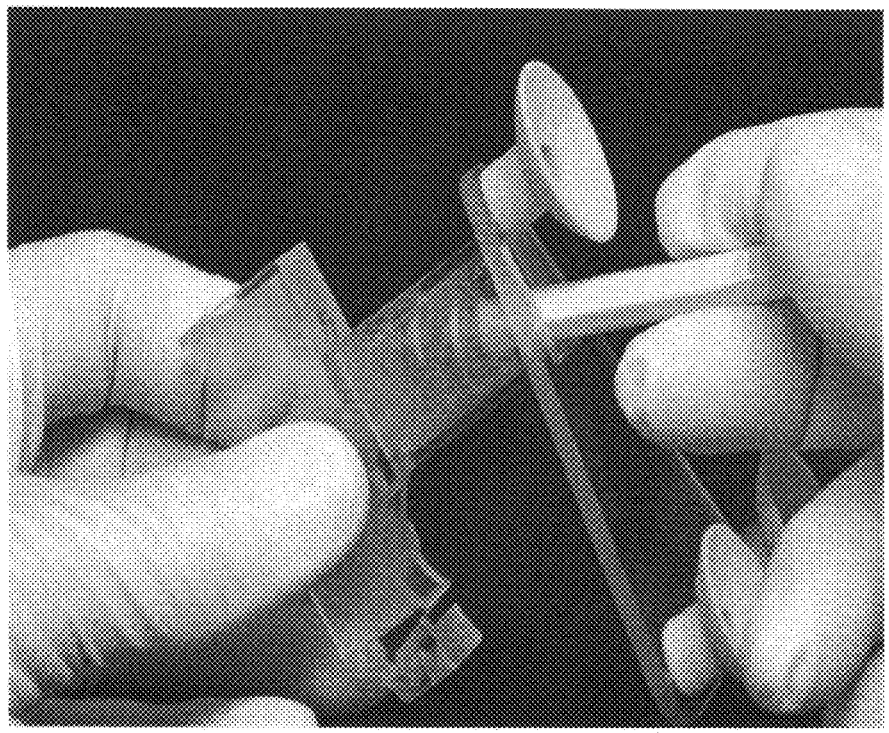
FIG. 18 shows the dispenser unit being disassembled or disengaged from the tower support for cleaning.

The dispensing unit and any of the other components can be cleaned as necessary. FIG. 18 shows the dispenser unit being disassembled or disengaged from the tower support for cleaning. A pencil is useful for manipulating the separation by bending back flexible latch 214 (FIGS. 7B and 7C) to release end 424 (FIG. 7C) of attachment element 422. All components can then be resterilized by steam autoclaving methods or by other means of sterilization.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention. It is therefore intended that such variations be included within the scope of the following claims and their equivalents.

We claim:

1. A lancet dispensing assembly for dispensing individual lancets from a stack of lancets, said assembly operative to dispense said individual lancets by one-handed manipulation by user of said assembly, comprising:
   a base component;
   a clip component for retaining a plurality of stacked individual lancets;
   a dispenser unit component, wherein said clip component is disposed within housing of said dispenser unit component and wherein an escapement element is disposed within said housing of said dispenser unit component, said escapement element operative to allow for lancets to be dispensed one at a time;
   a means for positioning said dispense unit component to allow for lancets to be dispensed; and
   a top weight component.

2. The assembly as described in claim 1 wherein said clip component retains said lancets within a cavity of said clip component.

3. The assembly as described in claim 1 wherein said individual lancets retained in said clip have a flat point 4.0-6.0 mm in length.

4. The assembly as described in claim 1 wherein said top weight component is positioned within housing of said dispenser unit component.

5. The assembly as described in claim 1 wherein said means for positioning allows said lancet dispensing assembly to be disassembled and reassembled.

6. The assembly as described in claim 1 wherein said means for positioning comprises an attachment element on the dispenser unit.

7. The assembly as described in claim 1 wherein said means for positioning comprises a flexible latch.

8. The assembly as described in claim 1 wherein said base component comprises a tower support for supporting said dispenser unit and displacing said dispenser unit from the bottom plate the base by a distance which allows for retrieval of lancets from said dispenser unit.

9. The assembly as described in claim 1 wherein said base component comprises a stability means to provide Stability during the dispensing process.

10. The assembly as described in claim 9, wherein said stability means is one or more suction cups, rubber matting, weights, or the like.

11. The assembly as described in claim 1 wherein the upper surface of said top weight component forms a groove.

12. The assembly as described in claim 1 wherein the entire lancet dispenser assembly can be sterilized as an entire unit and/or each component can be sterilized individually or in containers enclosing a plurality of components.

13. The assembly as described in claim 1 whereby lancets can be removed and reloaded easily by a user wearing gloves and using only one hand.

14. The assembly as described in claim 1 wherein the entire lancet dispenser assembly can be disassembled and reassembled.

15. A lancet dispensing assembly for dispensing individual lancets from a stack of lancets, said assembly operative to dispense said individual lancets by one-handed manipulation by user of said assembly, comprising:
   a base component;
   a clip component for retaining a plurality of stacked individual lancets;
   a dispenser unit component, wherein said clip component is disposed within housing of said dispenser unit component, said housing being comprised of a wider rectangular channel wherein said clip is positioned and a narrower rectangular channel wherein a portion of each individual lancet of a stack of lancets is positioned, said portion being that portion of the lancet not residing within the clip cavity and wherein an escapement element is disposed within said housing of said dispenser unit component, said escapement element operative to allow for lancets to be dispensed one at a time;
   a means for positioning said dispenser unit component to allow for lancets to be dispensed; and
   a top weight component.

16. A lancet dispensing assembly for dispensing individual lancets from a stack of lancets, said assembly operative to dispense said individual lancets by one-handed manipulation by user of said assembly, comprising:
   a base component;
   a clip component for retaining a plurality of stacked individual lancets;
   a dispenser unit component, wherein said clip component is disposed within housing of said dispenser unit component, said housing being comprised of a wider rectangular channel wherein said clip is positioned and a narrower rectangular channel wherein a portion of each individual lancet of a stack of lancets is positioned, said portion being that portion of the lancet not residing within the clip cavity and wherein an escapement element is disposed within said housing of said dispenser unit component, said escapement element operative to allow for lancets to be dispensed one at a time;
   a means for positioning said dispenser unit component to allow for lancets to be dispensed; and
   a top weight component, wherein said top weight component fits within said narrower channel of said dispenser unit housing.

17. A lancet dispensing asssembly for dispensing individual lancets from a stack of lancets, said assembly operative to dispense said individual lancets by one-handed manipulation by user of said assembly, comprising:
   a base component;
   a clip component for retaining a plurality of stacked individual lancets;
   a dispenser unit component, wherein said clip component is disposed within housing of said dispenser unit component and wherein an escapement element composed of rubber or a similar frictional material is disposed within said housing of said dispenser unit component, said escapement element operative to allow for lancets to be dispensed one at a time;
   a means for positioning said dispenser unit component to allow for lancets to be dispensed; and
   a top weight component.

18. A lancet dispensing assembly for dispensing individual lancets from a stack of lancets, said assembly operative to dispense said individual lancets by one-handed manipulation by user of said assembly, comprising:
   a base component;
   a clip component for retaining a plurality of stacked individual lancets, said clip component comprising a flexible latch;
   a dispenser unit component, wherein said clip component is disposed within housing of said dispenser unit component and wherein an escapement element is disposed within said housing of said dispenser unit component, said escapement element operative to allow for lancets to be dispensed one at a time;

a means for positioning said dispenser unit component to allow for lancets to be dispensed; and a top weight component.

19. A lancet dispensing assembly for dispensing individual lancets from a stack of lancets, said assembly operative to dispense said individual lancets by one-handed manipulation by user of said assembly, comprising:

a base component;

a clip component for retaining a plurality of stacked individual lancets, said clip component covered with a cover during sterilization and transport;

a dispenser unit component, wherein said clip component is disposed within housing of said dispenser unit component and wherein an escapement element is disposed within said housing of said dispenser unit component, said escapement element operative to allow for lancets to be dispensed one at a time;

a means for positioning said dispenser unit component to allow for lancets to be dispensed; and a top weight component.

* * * * *